United States Patent [19]

Brown et al.

US005750528A

[11] Patent Number: 5,750,528
[45] Date of Patent: May 12, 1998

[54] BLOCKADE OF NEURONAL M-CHANNELS AS A THERAPEUTIC APPROACH TO THE TREATMENT OF NEUROLOGICAL DISEASE

[75] Inventors: Barry Stephen Brown, Wilmington; Simon Piers Aiken, Greenville, both of Del.; Robert Zaczek, Avondale, Pa.; Paul Richard Hartig, Princeton, N.J.; Christopher Allan Teleha; Wendell Wilkie Wilkerson, both of New Castle, Del.; Richard Alan Earl, Wilmington, Del.

[73] Assignee: The DuPont Merck Pharmaceutical Company, Wilmington, Del.

[21] Appl. No.: 384,289

[22] Filed: Feb. 1, 1995

[51] Int. Cl.$^6$ .............. A61K 31/50; A61K 31/505; A61K 31/445; A61K 31/38

[52] U.S. Cl. .............. 514/253; 514/256; 514/315; 514/430; 514/449

[58] Field of Search .................. 514/253, 256, 514/315, 430, 449

[56] References Cited

U.S. PATENT DOCUMENTS 5,173,489  12/1992  Earl et al. ................... 514/252

FOREIGN PATENT DOCUMENTS

| 0311010 | 4/1989 | European Pat. Off. |
| WO 9314085 | 7/1993 | WIPO |
| WO 9314092 | 7/1993 | WIPO |
| WO 9424131 | 10/1994 | WIPO |

OTHER PUBLICATIONS

Lampe and Brown, *Electrophysiological Effects of DuP 996 on Hippocampal CA1 Neurons*, Soc. Neuroscience Abstr., 17 1588, Abstract #632.19 (1991).

Frey et al., *DuP996, a Novel Neurotransmitter Releaser, Blocks Voltage–Activated Potassium Currents in Cultured Neocortical Neurons*, Soc. Neuroscience Abstr., 17 1588, Abstract #632.20 (1991).

Aiken and Brown, *Linopirdine (DuP 996), A Neurotransmitter Release Enhancer, Blocks M–Current in Rat CA1 Hippocampal Neurons*, Biophy.J. 66:A210 (1994) Tu–Pos 410 and Brain Research Assoc. Abstracts 11:67, Abstract #17.200 (1994).

Maciag, et al., *Studies on the Role of K+, Cl–, and Na+ Ion Permeabilities in the Acetylcholine Release Enhancing Effects of Linopirdine (DuP 996) in Rat Cerebral Cortical Slices*, J. Pharmacol. Exper. Therapy, 271, 891–897 (1994).

Aiken, et al., *Reduction of Spike Fequency Adaptation and Blockade of M–Current in Rat CA1 Pyramidal Neurones by Linopirdine (DuP 996), a Neurotransmitter Release Enhancer*, Br.J.Pharmacol.115, 1163–1168 (1995).

*Primary Examiner*—Zohreh Fay

[57] ABSTRACT

Compounds which block neuronal M-channels are useful for treating conditions involving neurotransmitter deficiencies, traumatic brain injury, or the depressive phase of bipolar disorder. Compounds can be evaluated for utility in treating these conditions by determining whether they are capable of blocking neuronal M-channels.

7 Claims, No Drawings

5,750,528

BLOCKADE OF NEURONAL M-CHANNELS AS A THERAPEUTIC APPROACH TO THE TREATMENT OF NEUROLOGICAL DISEASE

FIELD OF INVENTION

This invention relates to treatment of neurological diseases involving neurotransmitter deficiencies, traumatic brain injury or the depressive phase of bipolar disorder by administration of compounds which block neuronal M-channels.

BACKGROUND OF THE INVENTION

Several neurological diseases are known to involve deficiencies in CNS neurotransmitter systems. Accordingly, cholinesterase inhibitors are used to alleviate the cholinergic deficit found in Alzheimer's disease. L-DOPA is used to supply dopamine precursor for the treatment of Parkinson's disease, and monoamine reuptake blockers are used to restore the noradrenergic and serotonergic deficits associated with depression. Another approach to the treatment of these diseases is to enhance the release of the deficient neurotransmitter or to mimic its action.

Linopirdine (3,3-bis(4-pyridinylmethyl)-1-phenylindolin-2-one) has been shown to enhance $K^+$-stimulated release of acetylcholine, dopamine and glutamate in the mammalian CNS. It has been reported that linopirdine, when tested for electrophysiological effects on rat hippocampal neurons, reduced spike frequency adaptation, possibly due to attenuation of certain $K^+$ conductances. Lampe, B. W. & Brown, B. S. (1991). Electrophysiological effects of DuP 996 on hippocampal CA1 neurons. *Soc. Neurosci. Abstr.*, 17, 1588.

Recent studies in our laboratories have shown that for linopirdine and several structural analogs there is a good correlation between block of M-current (a voltage dependent, receptor-sensitive outward potassium current) and enhancement of neurotransmitter release in vitro. It is known that several agents which activate muscarinic, metabotropic and serotonergic receptors lead to the block of M-current indirectly through activation of second messenger systems. However, because these actions are indirect and non-selective, activation of additional cellular mechanisms may underlie known cardiac and gastrointestinal side effects. In contrast, selective blockade of M-channels would result in pre-synaptic neurotransmitter release enhancement and augmentation of post-synaptic neurotransmitter effects, with minimal side effects resulting from activation of additional cellular mechanisms.

Although the pharmaceutical industry has targeted a variety of ion channels in development of therapeutic agents, the M-channel has not yet received attention. Located primarily in the brain, the physiological role of M-current is to suppress neuronal excitability. Blockade of M-current results in activation of neurotransmitter pathways. Agents which block M-channels would cause increases in neurotransmitter release and general brain excitation. These agents would, therefore, be useful in the treatment of neurological diseases involving either known neurotransmitter deficiencies (e.g., Alzheimer's disease, Parkinson's disease, depression, Huntington's disease), traumatic brain injury or the depressive phase of bipolar disorder.

U.S. Pat. No. 5,173,489 and European Patent Application Publication 0 311 010 A2 disclose linopirdine and analogs of formula I:

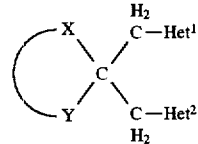

U.S. application Ser. No. 07/821,572, filed Jan. 16, 1992, and International Application Publication WO93/14085, published Jul. 23, 1993 disclose compounds of the formula II:

where Q is

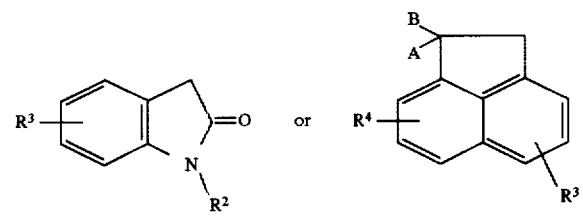

U.S. application Ser. No. 07/821,570, filed Jan. 16, 1992, and International Application Publication WO93/14092, published Jul. 22, 1993 disclose compounds of the formula III:

where Q is

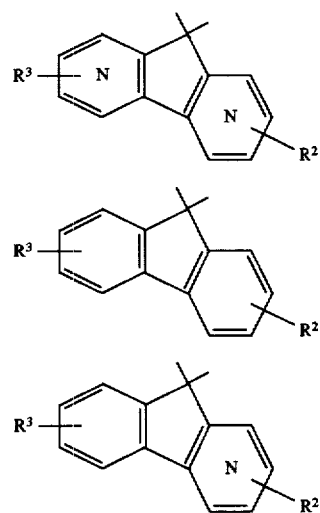

U.S. application Ser. No. 08/216881, filed Mar. 28, 1994, and International Application Publication WO94/24131, published Oct. 27, 1994, disclose compounds of the formula IV:

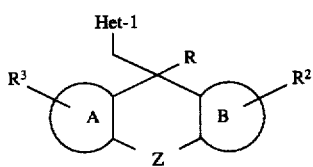

(IV)

Each of the above-identified U.S. patent and applications and European and International published applications states that the disclosed compounds stimulate the release of neurotransmitters and are useful in the treatment of cognitive deficiencies and/or neurological function deficits and/or mood and mental disturbances, in patients suffering from nervous system disorders like Alzheimer's disease, Parkinson's disease, senile-dementia, multi-infarct dementia, Huntington's disease, mental retardation, Myasthenia gravis, etc. The documents do not disclose that the actions of the compounds are mediated through neuronal M-channel blockade or that they can be used to treat traumatic brain injury or the depressive phase of bipolar disorder.

Compounds of the type covered by formulas I–III have been found to produce iatrogenic seizures in rats at doses of 100 mg/kg of body weight or less. Compounds of the type covered by formula IV have not been found to produce iatrogenic seizures at doses in this range.

SUMMARY OF THE INVENTION

In a first aspect, this invention is a method of evaluating a compound for utility in treating neurological diseases involving neurotransmitter deficiencies or traumatic brain injury or the depressive phase of bipolar disorder which comprises determining whether the compound is capable of blockade of neuronal M-channels.

In a second aspect, this invention is a method of treating a mammal suffering traumatic brain injury or the depressive phase of bipolar disorder which comprises administering to the mammal a compound which is capable of blockade of neuronal M-channels.

In a third aspect, this invention is a method of treating a mammal which has neurological disease involving neurotransmitter deficiency which comprises administering to the mammal a compound which is capable of blockade of neuronal M-channels without producing iatrogenic seizures.

DETAILED DESCRIPTION OF THE INVENTION

In one aspect, this invention is a method of evaluating a compound for utility in treating neurological diseases involving neurotransmitter deficiencies or traumatic brain injury or the depressive phase of bipolar disorder which comprises determining whether the compound is capable of blockade of neuronal M-channels.

Several standard methods are available for determining whether a compound is capable of blocking neuronal M-channels. Procedures for recording M-current which can be used in the practice of this invention are disclosed in the following publications, the entire disclosures of which are incorporated herein by reference: Adams, P. R., Brown, D. A. and Constanti, A. Pharmacological inhibition of the M-current. *J. Physiology* (London) 332: 223–262, 1982; Beech, D. J., Bernheim, L., Mathie, A. and Hille, B. Intracellular Ca2+ buffers disrupt muscarinic suppression of Ca2+ current and M-current in rat sympathetic neurons. *Proc. Natl. Acad. Sci.* USA 88: 652–656, 1991; Robbins, J., Trouslard, J., Marsh, S. J. and Brown, D. A. Kinetic and pharmacological properties of the M-current in rodent neuroblastoma×glioma hybrid cells. *J. Physiology* (London) 451: 169–185, 1992. These methods involve the following steps:

(1) perfusing neurons with a physiological perfusion solution containing $K^+$ and a substance to block $Na^+$ current;

(2) depolarizing a neuron from a holding potential of about −60 mV to about −70 mV to a potential of about −30 mV to −40 mV and measuring the amplitude of the M-current activated by the depolarization;

(3) adding test compound to the perfusion solution;

(4) repeating step (2); and (5) comparing the amplitudes of the M-currents produced in steps (2) and (4).

The specific method which we have used, involving recording M-currents in rat hippocampal slices, is described below.

Pathogen-free male CD rats from Charles River (Wilmington, Mass., U.S.A.), weighing 100–200 g, were anaesthetized with either halothane (2-bromo-2-chloro-1,1,1-trifluoroethane) or Metofane (2,2-dichloro-1,1-difluoroethylmethyl ether). After decapitation, the brain was rapidly excised and submerged in an ice-cold oxygenated physiological solution while one hippocampus was removed. Transverse slices (400 µm thick) were prepared on a Mollwain tissue chopper (Mickle Laboratory Engineering Co., Gomshall, Surrey), and transferred to a Perspex holding chamber (Medical Systems Corp., Greenvale, N.Y., U.S.A.) filled with an oxygenated physiological solution (room temperature, 23° C.). The physiological solution for both dissection and recording was of the following composition (mM): NaCl (127.0), $NaHCO_3$ (26.0), KCl (3.0), $CaCl_2$ (2.5), $NaH_2PO_4$ (1.25), $MgSO4$ (1.0) and glucose (10.0), gassed with 5% carbon dioxide in oxygen (pH 7.35).

Hippocampal slices were placed on a nylon mesh in a submersion-type recording chamber (Medical Systems), and pinned to the Sylgard base. Oxygenated physiological solution (23° C.) was superfused at 1–3 ml $min^{-1}$. A pellet of Ag/AgCl in the solution provided a reference ground. Microelectrodes were pulled from borosilicate glass (1.2 mm/0.68 mm outerlinner diameter; A-M Systems, Inc., Everett, Wash., U.S.A.) using a Sutter P-80/PC electrode puller (Sutter Instruments, Novato, Calif., U.S.A.). Resistances were 50–80MΩ when filled with 3M KCl for voltage-clamp recordings. Cell recordings were obtained by means of an Axoclamp-2A amplifier (Axon Instruments, Inc., Foster City, Calif., U.S.A.). A chloride-coated silver wire formed the bridge from electrode to headstage.

Impalements were obtained in bridge mode. The following criteria were used to decide the suitability of a neuron for recording: resting membrane potential (RMP) negative of −55 mV, input resistance >20MΩ (as measured at RMP by a 500 pA hyperpolarizing pulse), and action potentials (APs) that overshot 0 mV. In general, RMPs were negative of −60 mV and input resistances were >70MΩ. Having obtained a stable recording, TTX (tetradotoxin, Calbiochem, La Jolla, Calif., USA) (500 nM) was added to eliminate Na+ current. Cells were then voltage-clamped in discontinuous mode, using a 2.0 kHz switching frequency (30% duty cycle). The monitor output was observed on an oscilloscope to ensure adequate settling of the clamp. In between voltage-clamp protocols, RMP was monitored by chart recorder.

Specific $K^+$ currents were recorded by means of pCLAMP software (version 6.0.1, Axon Instruments), and each episode obtained represented the mean of 6–8 individual runs.

Membrane conductance, where required, was calculated by dividing the current response to a voltage step by the magnitude of that voltage step.

A two-tailed Student's t test for paired data was used to compare mean values for the amplitude of the slow afterhyperpolarization and M-current ($I_M$) amplitude and time constant, before and after test compound administration. A two-tailed Student's t test for paired data was also used to compare the effect of test compound on $I_M$ amplitude before and after administration of atropine. A P value <0.05 was considered to indicate a significant difference. Data values are expressed as mean±s.e.mean. Test compounds were synthesized and stock solutions (in 100 mM HCl or water) were prepared immediately before use. The stock solution was added directly to the superfusing solution. Application time for test compounds was usually 30 min.

$I_M$ was recorded in voltage-clamped neurons by stepping to –40 mV or –30 mV for one second (1s) from a holding potential of –70 mV, repolarizing by 20 mV for 1s, and then returning the cell to –40 mV or –30 mV for an additional 1s. $I_M$ is inactive at –70 mV, and is activated by the depolarization to –40 mV or –30 mV. When the cell is repolarized by 20 mV (i.e. to –60 mV or –50 mV, respectively), $I_M$ deactivates in a mono-exponential fashion, and can be seen as the slow component of the response following the mV repolarization. The amplitude of $I_M$ was measured by extrapolating this mono-exponential response to the time of the mV repolarization.

In a second aspect, this invention is a method of treating a mammal suffering from traumatic brain injury or the depressive phase of bipolar disorder which comprises administering to the mammal a compound which is capable of blocking neuronal M-channels.

Compounds which are capable of blockade of neuronal M-channels, as determined by the tests described above, include the following compounds of Formulas I–IV and their physiologically suitable hydrates and salts:

Compounds of Formula I

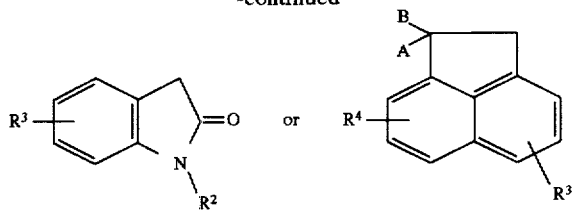

wherein:

X and Y taken together to form a saturated or unsaturated carbocyclic first ring and the shown carbon in said ring is alpha to at least one additional carbocyclic aromatic ring fused to the first ring, the total number of carbocyclic fused rings being 3–5, the sole heterocyclic substituents on said fused rings being $Het^1$ and $Het^2$;

one of $Het^1$ and $Het^2$ is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pridazinyl,
(e) 3, or 4-pyrazolyl,
(f) 2, or 3-tetrahydrofuranyl, and
(g) 3-thienyl.

Compounds of formula II

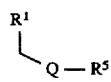

where Q is

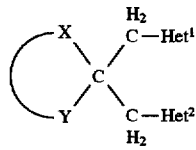

A and B are independently selected from the group consisting of H, $R^4$, OH, AND $OCOR^4$;

A and B together form =O, =S, =CH2, =$CHR^4$, =$C(R^4)$, =NOH, =$NOR^4$, 1,3 dioxane, 1,3-dioxolane, 1,3-dithiane or 1,3-dithiolane;

$R^1$ is 4-, 3-, or 2-pyridyl, pyrimidyl, pyrazinyl, 2-fluoro-4-pyridyl or 3-fluoro-4-pyridyl;

$R^2$ is alkyl of 1 to 10 carbon atoms, cyclalkyl of 3 to 8 carbon atoms, 4-, 3-, or 2-pyridyl, Phe or Phe-W;

Phe is a phenyl group;

W is F, Cl, Br, $R^4$, OH, $OR^4$, $NO_2$, $NH_2$, $NHR^4$, $NR^4R^4$, CN, $S(O)_mR^4$ $R^3$ is H, F, Cl, Br, CN, OH, $NO_2$, $NH_2$, $CF_3$, $NHR^4$, $NR^4R^4$, $R^4$, $OR^4$, $S(O)_mR^4$ $R^4$ and $R^{4'}$ are alkyl of 1 to 4 carbon atoms, $CH_2$-Phe-W or Phe-W;

$R^5$ is $(CH_2)_n$—Y or $OCOR^4$;

Y is H, OH, $NH_2$, $NHR^4$, $NR^4R^4$, $NHCOR^4$, $NHCO_2R^4$, F, Cl, Br, $OR^4$, $S(O)_mR^4$, $CO_2H$, $CO_2R^4$, CN, $CONR^4R^4$, $CONHR^4$, CONH2, $COR^4$, CH=$CHCO_2R^4$, $OCOR^4$, Phe, Phe-W, C≡$CCO_2R^4$ or C≡$CR^4$;

m is 0,1 or 2;

n is 1 to 7;

provided that, when Q is oxindole and R5 is (CH2)nY, then Y is other than OH.

Compounds of formula III

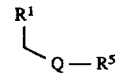

where Q is

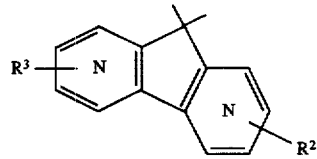

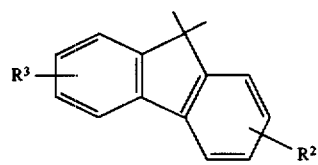

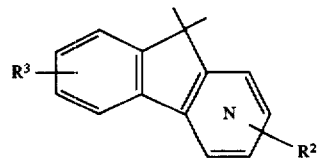

$R^1$ is 4-, 3-, or 2-pyridyl, pyrimidyl, pyrazinyl, 2-fluoro-4-pyridyl;

$R^2$ and $R^3$ are independently H, F, Cl, Br, $NO_2$, OH, $R^4$, $OR^4$, $CO_2R^4$, $COR^4$, $CONH_2$, $CONHR^4$, $CONR^4R^4$, $S(O)_mR^4$, $NH_2$, $CF_3$, $NHR^4$ $NR^4R^4$;

$R^4$ and $R^{4'}$ are independently H, alkyl of 1 to 4 carbon atoms, $CH_2$Phe-W or Phe-W;

Phe is a phenyl group;

$R^5$ is $(CH_2)_n$—Y or $OCOR^4$;

Y is H, OH, $NH_2$, $NHR^4$, $NR^4R^4$, $NHCOR^4$, $NHCO_2R^4$, $NH_2S(O)_2R^4$, F, Cl, Br, $OR^4$, $S(O)_mR^4$, $CO_2H$, $CO_2R^4$, CN, $CONR^4R^4$, $CONHR^4$, $CONH_2$, $COR^4$, $CH=CHCO_2R^4$, $OCOR^4$, Phe, Phe-W, $C\equiv CCO_2R^4$, $CH=CHR^4$ or $C\equiv CR^4$;

W is F, Cl, Br, $R^4$, $OR^4$, $NO_2$, $NH_2$, $NHR^4$, $NR^4R^4$, CN or $S(O)_mR^4$;

m is 0, 1 or 2, n is 1 to 7.

Compounds of formula IV

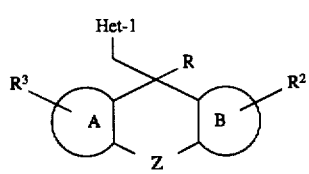

(IV)

wherein:

A is an aromatic or heteroaromatic ring selected from the group consisting of:

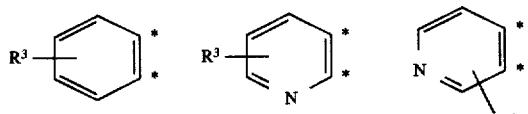

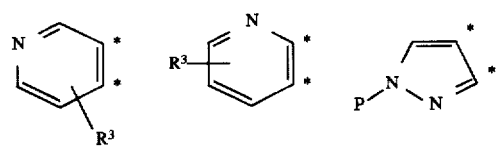

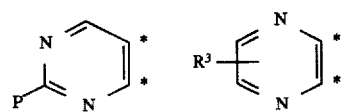

B is an aromatic or heteroaromatic ring selected from the group consisting of:

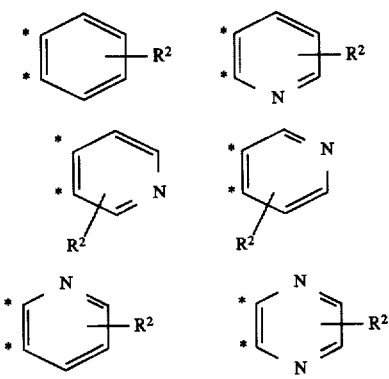

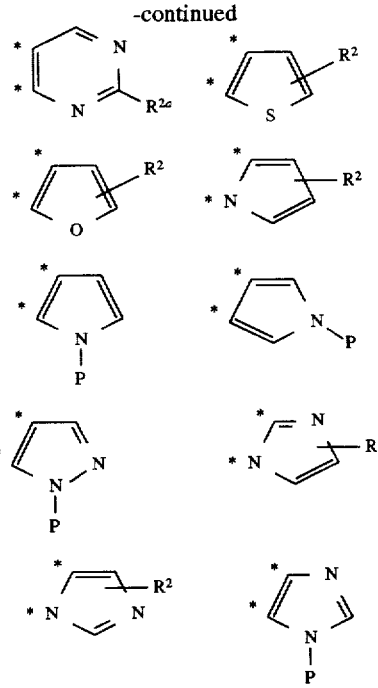

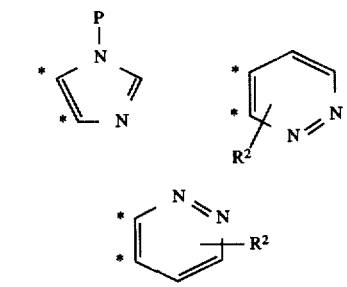

Z is a bond, —C(=O)—, —O—, —NP—, —S—, —S(=O)— or —$SO_2$—;

P is H, phenyl, $C_1$–$C_4$ alkyl or benzyl $R^2$ and $R^3$ are independently H, F, Cl, Br, I, $CF_3$, OH, $R^4$, —$(CH_2)_nC\equiv CR^5$, —$OR^4$, $NR^6R^{6a}$, —$CO_2R^4$, —$COR^4$, —$CONH_2$, —$CONHR^4$, —$CONR^4R^{4a}$, —$(CH_2)_nNR^6COR^4$ or —$S(O)_mR^4$;

$R^{2a}$ is H, $C_1$–$C_4$ alkyl or phenyl;

m is 0, 1, or 2;

$R^4$ and $R^{4a}$ are independently alkyl of 1 to 4 carbons;

each of Het-1 and Het-2 is independently a heterocycle selected from the group consisting of:

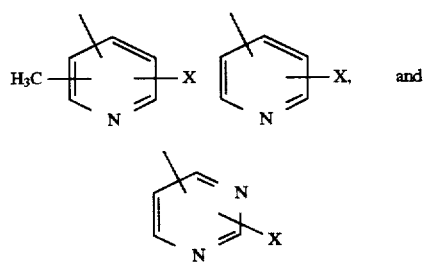

each X is independently H, F, Cl, Br, I, $CF_3$, $OR^4$, $NR^6R^{6a}$, $NO_2$, or CN R is selected from the group consisting of:

H, —CH$_2$-Phe-W, —CH$_2$-(Het-2), —(CH$_2$)$_n$—O—COR$^5$, —(CH$_2$)$_n$—CH=CH—R$^5$, —(CH$_2$)$_n$—C≡C—R$^5$, —(CH$_2$)$_n$—Y;

W is H, F, Cl, Br, —CN, CO$_2$R$^5$, R$^4$, OR$^4$, S(O)$_m$—R$^4$;

Y is —OR$^6$, NHR$^6$, NR$^6$R$^{6a}$, NHCOR$^6$, NHCO$_2$R$^6$, CO$_2$R$^6$, —CN, CONHR$^6$, CONR$^6$R$^{6a}$, —COR$^6$, —CH$_2$—CH=CHCO$_2$R$^6$, —OCOR$^6$, or CO$_2$Bz; and n is 1 to 5;

R$^5$, R$^6$ and R$^{6a}$ are independently H or alkyl of 1 to 6 carbons.

with the proviso that when A is a 6-membered aromatic or heteroaromatic ring, Het-1 and Het-2 are not both selected from

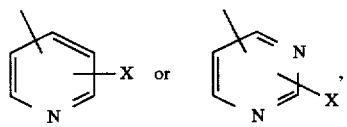

when X is H.

Compounds of Formula I are disclosed in U.S. Pat. No. 5,173,489 and European Patent Application Publication 0 311 010 A2. Compounds of Formula II are disclosed in U.S. application Ser. No. 07/821,572 and International Application Publication WO 93/14085. Compounds of Formula III are disclosed in U.S. application Ser. No. 07/821,670 and International Application Publication WO 93/14092. Compounds of formula IV are disclosed in United States application Ser. No. 08/216881 and International Application Publication WO 94/24131. The entire disclosures of the documents mentioned in this paragraph are incorporated herein by reference. The disclosures in those documents relating to formulations, dosages, and routes of administration of compounds of formulas I–IV for treatment of diseases involving neurotransmitter deficiencies are equally applicable to the present invention for treatment of traumatic brain injury or the depressive phase of bipolar disorder.

Preferred compounds for treatment of traumatic brain injury or the depressive phase of bipolar disorder in accordance with the second aspect of this invention are compounds which block neuronal M-channels without producing iatrogenic seizures at doses within the therapeutic range of 0.001 to 100 mg/kg of body weight, such as compounds of formula IV above.

In a third aspect, this invention is a method of treating a mammal which has a neurological disease involving neurotransmitter deficiency which comprises administering to the mammal a compound which is capable of blockade of neuronal M-channels without producing iatrogenic seizures. Compounds which can be used for practice of this aspect of the invention include compounds of formula IV above and their physiologically suitable hydrates and salts, in the formulations, dosages, and routes of administration described in U.S. Ser. No. 08/216881 and WO 94/24131.

Preferred compounds of formula IV for use in both the second and third aspects of this invention are compounds wherein:

A is a six member aromatic or heteroaromatic ring selected from the group consisting of:

B is an aromatic or heteroaromatic ring selected from the group consisting of:

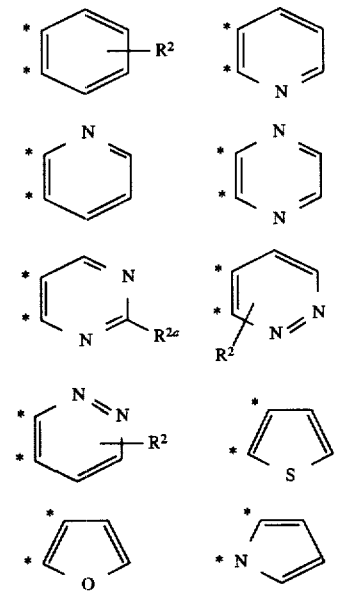

R$^2$ is H, I, R$^4$, —C≡CH, —OR$^4$, —NR$^6$R$^{6a}$, —CO$_2$R$^4$, or —(CH$_2$)$_n$NR$^6$COR$^4$;

R$^3$ is H;

Het-1 and Het-2 are independently

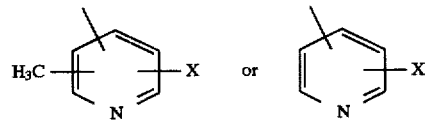

X is H, F, Cl, Br, or OR$^4$;

R is selected from the group consisting of:

H, 3-cyanobenzyl-, —CH2-(Het-2), —(CH$_2$)$_1$—CO$_2$Et, —(CH$_2$)$_3$—CO$_2$Et, —(CH$_2$)$_4$—OCOCH$_3$, —(CH$_2$)$_4$—CONH$_2$, benzyl, —(CH$_2$)$_4$—OH, and —(CH$_2$)$_4$—CN.

Specific preferred compounds of formula IV for use in both the second and third aspects of this invention are the following:

(a) 4-(4-Pyridinylmethyl)-4H-indeno[1,2-B]thiophene;

(b) 4-(4-Pyridinylmethyl)-4H-indeno[1,2-B]thiophene-4-pentanenitrile Hydrobromide Hydrate;

(c) 4-(4-Pyridinylmethyl)-4H-indeno[1,2-B]thiophene-4-acetic acid Ethyl Ester Hydrochloride;

(d) 4-(4-Pyridinylmethyl)-4H-indeno[1,2-B]thiophene-4-butanol Acetate (Ester) Hydrochloride;

(e) 4-(4-Pyridinylmethyl)-4H-indeno[1,2-B]thiophene-4-pentanamide Hydrochloride Hydrate;

(f) 2-Fluoro-4-[4-(4-pyridinylmethyl)-4H-indeno[1,2-B]thiophen-4-ylmethyl]-pyridine;

(g) 4-[4-(Phenyl)-4H-indeno[1,2-B]thiophen-4-ylmethyl]-pyridine;

(h) 4-(4-Pyridinylmethyl)-4H-indeno[1,2-B]thiophene-4-butanol;

(i) 4-(4-Pyridinylmethyl)-4H-thieno[2',3':3,4]cyclopenta[1,2-B]pyridine;

(j) 4-[(2-Fluoro-4-pyridinyl)methyl]-4-(4-pyridinylmethyl)-4H-thieno[3',2':4,5]cyclopenta[1,2-B]pyridine;

(k) 1,4-Dihydro-1-(phenylmethyl)-4,4-bis(4-pyridinylmethyl)-indeno[1,2-C]pyrazole;

(l) 2,4-Dihydro-2-phenyl-4,4-bis(4-pyridinylmethyl)-pyrazolo[4,3-B]pyrrolizine.

(m) 9,9-Bis((2-fluoro-4-pyridinyl)methyl)-2-hydroxy-9H-fluorene;

(n) 5-(2-Fluoro-4-pyridinyl)methyl)-5-(4-pyridinylmethyl)-5H-indeno[1,2-b]pyridine;

(o) 5-(2-Fluoro-4-pyridinyl)methyl)-5-(4-pyridinylmethyl)-5H-indeno[2,1-b]pyridine;

(p) 10,10-Bis((2-fluoro-4-pyridinyl)methyl)-9(10H)-anthracenone;

(q) 9-((2-Fluoro-4-pyridinyl)methyl)-9-(4-pyridinylmethyl)-9H-xanthene;

(r) 10-((2-Fluoro-4-pyridinyl)methyl)-10-(4-pyridinylmethyl)-9(10H)-anthracenone;

(s) 9,9-Bis((2-fluoro-4-pyridinyl)methyl)-4-azaxanthene;

(t) 5,5-Bis((2-fluoro-4-pyridinyl)methyl)-5H-indeno[1,2-b]pyridine;

(u) 4,4-Bis((2-fluoro-4-pyridinyl)methyl)-4H-thieno[3',2':4,5]cyclopenta[1,2-b]pyridine;

(v) 9-((2-Fluoro-4-pyridinyl)methyl)-9-(4-pyridinylmethyl)-4-azaxanthene;

(w) 9,9-Bis((2-fluoro-4-pyridinyl)methyl)-2-methoxyfluorene;

(x) 9,9-Bis((2-fluoro-4-pyridinyl)methyl)-7-methoxy-4-azaxanthene;

(y) 10,10-Bis((2-fluoro-4-pyridinyl)methyl)-3-hydroxy-9(10H)-anthracenone;

(z) 10,10-Bis((2-fluoro-4-pyridinyl)methyl)-2,6-dimethoxy-9(10H)-anthracenone;

(aa) 9,9-Bis((2-fluoro-4-pyridinyl)methyl)-cyclopenta[1,2-b:3,4-b']dipyridine;

(bb) 5,5-Bis((2-fluoro-4-pyridinyl)methyl)-2-phenyl-5H-indeno[1,2-d]pyrimidine;

(cc) 10,10-Bis((2-fluoro-4-pyridinyl)methyl)-3-methoxy-9(10H)-anthracenone;

(dd) 9,9-Bis((2-fluoro-4-pyridinyl)methyl)-9H-indeno[2,1-b]pyridine;

(ee) 5,5-Bis((2-fluoro-4-pyridinyl)methyl)-7-(ethynyl)-5H-indeno-[1,2-b]pyridine;

(ff) 9,9-Bis((2-fluoro-4-pyridinyl)methyl)-9H-indeno-[1,2-b]pyrazine;

(gg) 5,5-Bis((2-fluoro-4-pyridinyl)methyl)-5H-indeno-[1,2-d]pyrimidine;

(hh) 5,5-Bis((2-bromo-4-pyridinyl)methyl)-5H-indeno-[1,2-b]pyridine;

(ii) 9,9-Bis((2-fluoro-4-pyridinyl)methyl)-2-((N-methylamino)methyl)fluorene;

(jj) 9,9-Bis((2-fluoro-4-pyridinyl)methyl)-2-((N-methyl-N-methoxycarbonylamino)methyl)fluorene;

(kk) 9,9-Bis((2-fluoro-4-pyridinyl)methyl)-2-((N-methyl-N-acetylamino)methyl)fluorene;

(ll) 10,10-Bis((2-bromo-4-pyridinyl)methyl)-9(10H)-anthracenone;

(mm) 5,5-Bis((2-chloro-4-pyridinyl)methyl)-5H-indeno-[1,2-b]pyridine;

(nn) 5,5-Bis((2-fluoro-4-pyridinyl)methyl)-2-methyl-5H-indeno-[1,2-d]pyrimidine;

(oo) 5,5-Bis((2-methoxy-4-pyridinyl)methyl)-5H-indeno-[1,2-b]pyridine;

(pp) 5,5-Bis((2-fluoro-4-pyridinyl)methyl)-7-(ethyl)-5H-indeno-[1,2-b]pyridine;

(qq) 5,5-Bis((2-chloro-6-methyl-4-pyridinyl)methyl)-5H-indeno-[1,2-b]pyridine;

(rr) 5,5-Bis((2-methyl-4-pyridinyl)methyl)-5H-indeno-[1,2-b]pyridine;

(ss) 5,5-Bis((2-fluoro-4-pyridinyl)methyl)-7-(iodo)-5H-indeno-[1,2-b]pyridine;

(tt) 9,9-Bis((2-fluoro-4-pyridinyl)methyl)-9H-fluorene-1-carboxylic acid, methyl ester;

(uu) 9-((2-Fluoro-4-pyridinyl)methyl)-9-(4-pyridinylmethyl)-9H-fluorene-1-carboxylic acid, methyl ester, racemic;

(vv) 9,9-Bis((2-fluoro-4-pyridinyl)methyl)-9H-fluoren-1-amine;

(ww) 5,5-Bis((2-fluoro-4-pyridinyl)methyl)-5H-cyclopenta[2,1-b:3,4-b']dipyridine;

(xx) 5-((2-Fluoro-4-pyridinyl)methyl)-5-(4-pyridinylmethyl)-5H-cyclopenta[2,1-b:3,4-b']dipyridine-4-carboxylic acid, methyl ester, dihydrochloride salt (racemic);

(yy) 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (−)-isomer;

(zz) 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (+)-isomer;

(ab) 5,5-Bis((6-fluoro-3-pyridinyl)methyl)-5H-cyclopenta[2,1-b:3,4-b']dipyridine;

(ac) 5-((6-Fluoro-2-pyridinyl)methyl)-5-(4-pyridinylmethyl)-5H-cyclopenta[2,1-b:3,4-b']dipyridine;

(ad) 5,5-Bis((6-fluoro-2-pyridinyl)methyl)-5H-cyclopenta[2,1-b:3,4-b']dipyridine;

(ae) 5,5-Bis((3-methyl-4-pyridinyl)methyl)-5H-cyclopenta[2,1-b:3,4-b']dipyridine, trihydrochloride salt;

(af) 2-Fluoro-4-((9-(4-pyridinylmethyl)-9H-fluoren-9-yl)methyl)pyridine, hydrochloride salt;

(ag) 5-((2-Fluoro-4-pyridinyl)methyl)-5-(4-pyridinylmethyl)-5H-cyclopenta[2,1-b:3,4-b']dipyridine;

(ah) 5,5-Bis((2-fluoro-4-pyridinyl)methyl)thioxanthene-10,10-dioxide;

(ai) 5,5-Bis((2-fluoro-4-pyridinyl)methyl)thioxanthene-10-oxide;

(aj) 2,6-Dimethyl-4-((9-(4-pyridinylmethyl)-9H-fluoren-9-yl)methyl)pyridine, dihydrochloride salt;

(ak) 5-((2,6-Dimethyl-4-pyridinyl)methyl)-5-(4-pyridinylmethyl)-5H-cyclopenta[2,1-b:3,4-b']dipyridine;

(al) 5,5-Bis((2,6-dimethyl-4-pyridinyl)methyl)-5H-cyclopenta[2,1-b:3,4-b']dipyridine, E-2-butendiaote salt.

What is claimed:

1. A method of evaluating a compound for utility in treating neurological diseases involving neurotransmitter deficiencies or traumatic brain injury or the depressive phase of bipolar disorder which comprises:

(a) perfusing hippocampal neurons with a physiological perfusion solution containing K+ and a substance to block Na+ current and measuring the amplitude of the M-current through the neurons when the voltage is changed from one in the range of −30 to −40 mV to one in the range of −60 to −70 mV:

(b) adding a candidate compound for blocking neuronal M-channels to said solution and again measuring the amplitude of the M-current through the neurons over the same voltage change as in step 1: and (c) comparing the difference in amplitude of the M-current between that measured in step 1 and in step 2.

2. A method of treating a mammal which is suffering from traumatic brain injury or the depressive phase of bipolar disorder which comprises administering to the mammal a therapeutically effective amount of a compound which is capable of blockade of neuronal M-channels.

3. Method of claim 2 wherein the compound administered is capable of blockade of neuronal M-channels without producing iatrogenic seizures.

4. Method of claim 3 wherein the compound administered is a comound of formula IV:

(IV)

or a pharmaceutically acceptable salt or prodrug thereof wherein:

A is an aromatic or heteroaromatic ring selected from the group consisting of:

B is an aromatic or heteroaromatic ring selected from the group consisting of:

Z is a bond, —C(=O)—, —O—, —NP—, —S—, —S(=O)— or —SO$_2$—;

P is H, phenyl, C$_1$–C$_4$ alkyl or benzyl

R$^2$ and R$^3$ are independently H, F, Cl, Br, I, CF$_3$, OH, R$^4$, —(CH$_2$)$_n$C≡CR$^5$, —OR$^4$, NR$^6$R$^{6a}$, —CO$_2$R$^4$, —COR$^4$, —CONH$_2$, —CONHR$^4$, —CONR$^4$R$^{4a}$, —CH$_2$)$_n$NR$^6$COR$^4$ or —S(O)$_m$R$^4$;

R$^{2a}$ is H, C$_1$–C$_4$ alkyl or phenyl;

m is 0, 1, or 2;

R$^4$ and R$^{4a}$ are independently alkyl of 1 to 4 carbons;

each of Het-1 and Het-2 is independently a heterocycle selected from the group consisting of:

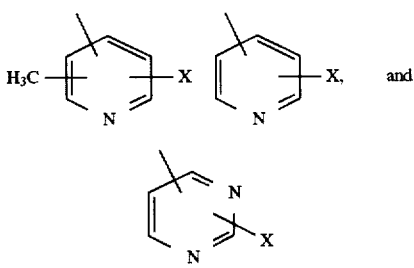

each X is independently H, F, Cl, Br, I, CF$_3$, OR$^4$, NR$^6$R$^{6a}$, NO$_2$, or CN R is selected from the group consisting of:
H, —CH$_2$-Phe-W, —CH$_2$-(Het-2), —(CH$_2$)$_n$—O—COR$^5$, —(CH$_2$)$_n$—CH=CH—R$^5$, —(CH$_2$)$_n$C≡CR$^5$, —(CH$_2$)$_n$—Y;

W is H, F, Cl, Br, —CN, CO$_2$R$^5$, R$^4$, OR$^4$, S(O)$_m$—R$^4$;
Y is —OR$^6$, NHR$^6$, NR6R$^{6a}$, NHCOR$^6$, NHCO$_2$R$^6$, CO$_2$R$^6$, —CN, CONHR$^6$, CONR$^6$R$^{6a}$, —COR$^6$, —CH$_2$—CH=CHCO$_2$R$^6$, —OCOR$^6$, or CO$_2$Bz; and
n is 1 to 5;

R$^5$, R$^6$ and R$^{6a}$ are independently H or alkyl of 1 to 6 carbons.

provided that when A is a 6-membered aromatic or heteroaromatic ring, Het-1 and Het-2 are not both selected from

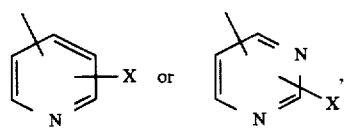

when X is H.

5. Method of claim 4 wherein the compound is administered at a dosage in the range of 0.001 to 100 mg/kg of body weight.

6. Method of claim 5 wherein, in formula IV

A is a six member aromatic or heteroaromatic ring selected from the group consisting of:

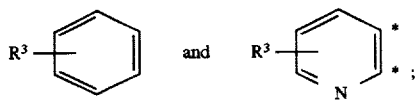

B is an aromatic or heteroaromatic ring selected from the group consisting of:

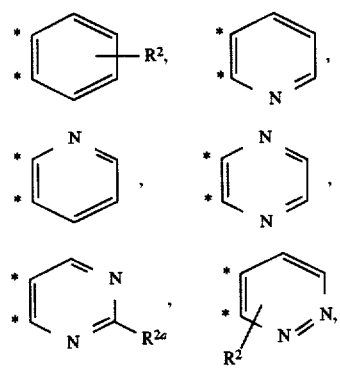

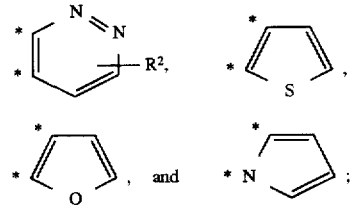

R$^2$ is H, I, R$^4$, —C≡—CH, —OR$^4$, —NR$^6$R$^{6a}$, —CO$_2$R$^4$, or —CH$_2$)$_n$NR$^6$COR$^4$;

R$^3$ is H;

Het-1 and Het-2 are independently

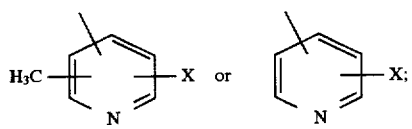

X is H, F, Cl, Br, or OR$^4$;

R is selected from the group consisting of:
H, 3-cyanobenzyl-, —CH$_2$-(Het-2), —(CH$_2$)$_1$—CO$_2$Et, —(CH$_2$)$_3$—CO$_2$Et, —(CH$_2$)$_4$—OCOCH$_3$, —(CH$_2$)$_4$—CONH$_2$, benzyl, —(CH$_2$)$_4$—OH, and —(CH$_2$)$_4$—CN.

7. Method of claim 6 wherein the compound administered is selected from the group consisting of:

(a) 4-(4-Pyridinylmethyl)-4H-indeno[1,2-B]thiophene;

(b) 4-(4-Pyridinylmethyl)-4H-indeno[1,2-B]thiophene-4-pentanenitrile Hydrobromide Hydrate;

(c) 4-(4-Pyridinylmethyl)-4H-indeno[1,2-B]thiophene-4-acetic acid Ethyl Ester Hydrochloride;

(d) 4-(4-Pyridinylmethyl)-4H-indeno[1,2-B]thiophene-4-butanol Acetate (Ester) Hydrochloride;

(e) 4-(4-Pyridinylmethyl)-4H-indeno[1,2-B]thiophene-4-pentanamide Hydrochloride Hydrate;

(f) 2-Fluoro-4-[4-(4-pyridinylmethyl)-4H-indeno[1,2-B]thiophen-4-ylmethyl]-pyridine;

(g) 4-[4-(Phenyl)-4H-indeno[1,2-B]thiophen-4-ylmethyl]-pyridine;

(h) 4-(4-Pyridinylmethyl)-4H-indeno[1,2-B]thiophene-4-butanol;

(i) 4-(4-Pyridinylmethyl)-4H-thieno[2',3':3,4]cyclopenta[1,2-B]pyridine;

(j) 4-[(2-Fluoro-4-pyridinyl)methyl]-4-(4-pyridinylmethyl)-4H-thieno[3',2':4,5]cyclopenta[1,2-B]pyridine;

(k) 1,4-Dihydro-1-(phenylmethyl)-4,4-bis(4-pyridinylmethyl)-indeno[1,2—C]pyrazole; and (l) 2,4-Dihydro-2-phenyl-4,4-bis(4-pyridinylmethyl)-pyrazolo[4,3-B]pyrrolizine.

(m) 9,9-Bis((2-fluoro-4-pyridinyl)methyl)-2-hydroxy-9H-fluorene;

(n) 5-(2-Fluoro-4-pyridinyl)methyl)-5-(4-pyridinylmethyl)-5H-indeno[1,2-b]pyridine;

(o) 5-(2-Fluoro-4-pyridinyl)methyl)-5-(4-pyridinylmethyl)-5H-indeno[2,1-b]pyridine;

(p) 10,10-Bis((2-fluoro-4-pyridinyl)methyl)-9(10H)-anthracenone;

(q) 9-((2-Fluoro-4-pyridinyl)methyl)-9-(4-pyridinylmethyl)-9H-xanthene;

(r) 10-((2-Fluoro-4-pyridinyl)methyl)-10-(4-pyridinylmethyl)-9(10H)-anthracenone;

(s) 9,9-Bis((2-fluoro-4-pyridinyl)methyl)-4-azaxanthene;

(t) 5,5-Bis((2-fluoro-4-pyridinyl)methyl)-5H-indeno[1,2-b]pyridine;

(u) 4,4-Bis((2-fluoro-4-pyridinyl)methyl)-4H-thieno[3',2':4,5]cyclopenta[1,2-b]pyridine;

(v) 9-((2-Fluoro-4-pyridinyl)methyl)-9-(4-pyridinylmethyl)-4-azaxanthene;

(w) 9,9-Bis((2-fluoro-4-pyridinyl)methyl)-2-methoxyfluorene;

(x) 9,9-Bis((2-fluoro-4-pyridinyl)methyl)-7-methoxy-4-azaxanthene;

(y) 10,10-Bis((2-fluoro-4-pyridinyl)methyl)-3-hydroxy-9(10H)-anthracenone;

(z) 10,10-Bis((2-fluoro-4-pyridinyl)methyl)-2,6-dimethoxy-9(10H)-anthracenone;

(aa) 9,9-Bis((2-fluoro-4-pyridinyl)methyl)-cyclopenta[1,2-b:3,4-b']dipyridine;

(bb) 5,5-Bis((2-fluoro-4-pyridinyl)methyl)-2-phenyl-5H-indeno[1,2-d]pyrimidine;

(cc) 10,10-Bis((2-fluoro-4-pyridinyl)methyl)-3-methoxy-9(10H)-anthracenone;

(dd) 9,9-Bis((2-fluoro-4-pyridinyl)methyl)-9H-indeno[2,1-b]pyridine;

(ee) 5,5-Bis((2-fluoro-4-pyridinyl)methyl)-7-(ethynyl)-5H-indeno-[1,2-b]pyridine;

(ff) 9,9-Bis((2-fluoro-4-pyridinyl)methyl)-9H-indeno-[1,2-b]pyrazine;

(gg) 5,5-Bis((2-fluoro-4-pyridinyl)methyl)-5H-indeno-[1,2-d] pyrimidine;

(hh) 5,5-Bis((2-bromo-4-pyridinyl)methyl)-5H-indeno-[1,2-b] pyridine;

(ii) 9,9-Bis((2-fluoro-4-pyridinyl)methyl)-2-((N-methylamino)methyl)fluorene;

(jj) 9,9-Bis((2-fluoro-4-pyridinyl)methyl)-2-((N-methyl-N-methoxycarbonylamino)methyl)fluorene;

(kk) 9,9-Bis((2-fluoro-4-pyridinyl)methyl)-2-((N-methyl-N-acetylamino)methyl)fluorene;

(ll) 10,10-Bis((2-bromo-4-pyridinyl)methyl)-9(10H)-anthracenone;

(mm) 5,5-Bis((2-chloro-4-pyridinyl)methyl)-5H-indeno-[1,2-b]pyridine;

(nn) 5,5-Bis((2-fluoro-4-pyridinyl)methyl)-2-methyl-5H-indeno-[1,2-d]pyrimidine;

(oo) 5,5-Bis((2-methoxy-4-pyridinyl)methyl)-5H-indeno-[1,2-b]pyridine;

(pp) 5,5-Bis((2-fluoro-4-pyridinyl)methyl)-7-(ethyl)-5H-indeno-[1,2-b]pyridine;

(qq) 5,5-Bis((2-chloro-6-methyl-4-pyridinyl)methyl)-5H-indeno-[1,2-b]pyridine;

(rr) 5,5-Bis((2-methyl-4-pyridinyl)methyl)-5H-indeno-[1,2-b]pyridine;

(ss) 5,5-Bis((2-fluoro-4-pyridinyl)methyl)-7-(iodo)-5H-indeno-[1,2-b]pyridine;

(tt) 9,9-Bis((2-fluoro-4-pyridinyl)methyl)-9H-fluorene-1-carboxylic acid, methyl ester;

(uu) 9-((2-Fluoro-4-pyridinyl)methyl)-9-(4-pyridinylmethyl)-9H-fluorene-1-carboxylic acid, methyl ester, racemic;

(vv) 9,9-Bis((2-fluoro-4-pyridinyl)methyl)-9H-fluoren-1-amine;

(ww) 5,5-Bis((2-fluoro-4-pyridinyl)methyl)-5H-cyclopenta[2,1-b:3,4-b']dipyridine;

(xx) 5-((2-Fluoro-4-pyridinyl)methyl)-5-(4-pyridinylmethyl)-5H-cyclopenta[2,1-b:3,4-b']dipyridine-4-carboxylic acid, methyl ester, dihydrochloride salt (racemic);

(yy) 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (−)-isomer;

(zz) 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (+)-isomer;

(ab) 5,5-Bis((6-fluoro-3-pyridinyl)methyl)-5H-cyclopenta[2,1-b:3,4-b']dipyridine;

(ac) 5-((6-Fluoro-2-pyridinyl)methyl)-5-(4-pyridinylmethyl)-5H-cyclopenta[2,1-b:3,4-b']dipyridine;

(ad) 5,5-Bis((6-fluoro-2-pyridinyl)methyl)-5H-cyclopenta[2,1-b:3,4-b']dipyridine;

(ae) 5,5-Bis((3-methyl-4-pyridinyl)methyl)-5H-cyclopenta[2,1-b:3,4-b']dipyridine, trihydrochloride salt;

(af) 2-Fluoro-4-((9-(4-pyridinylmethyl)-9H-fluoren-9-yl)methyl)pyridine, hydrochloride salt;

(ag) 5-((2-Fluoro-4-pyridinyl)methyl)-5-(4-pyridinylmethyl)-5H-cyclopenta[2,1-b:3,4-b']dipyridine;

(ah) 5,5-Bis((2-fluoro-4-pyridinyl)methyl)thioxanthene-10,10-dioxide;

(ai) 5,5-Bis((2-fluoro-4-pyridinyl)methyl)thioxanthene-10-oxide;

(aj) 2,6-Dimethyl-4-((9-(4-pyridinylmethyl)-9H-fluoren-9-yl)methyl)pyridine, dihydrochloride salt;

(ak) 5-((2,6-Dimethyl-4-pyridinyl)methyl)-5-(4-pyridinylmethyl)-5H-cyclopenta[2,1-b:3,4-b']dipyridine;

(al) 5,5-Bis((2,6-dimethyl-4-pyridinyl)methyl)-5H-cyclopenta[2,1-b:3,4-b']dipyridine, E-2-butendiaote salt.

\* \* \* \* \*